US00PP08026P

United States Patent [19]

Zaiger et al.

[11] Patent Number: Plant 8,026

[45] Date of Patent: Nov. 10, 1992

[54] INTERSPECIFIC TREE "FLAVOR KING"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 712,963

[22] Filed: Jun. 10, 1991

[51] Int. Cl.[5] ..... A01H 5/00

[52] U.S. Cl. ..... Plt./38.1

[58] Field of Search ..... Plt./38.1

*Primary Examiner*—James R. Feyrer

[57] ABSTRACT

A new and distinct variety of interspecific (Plum×-Plum Cot) tree which has the following unique combination of desirable features:

1. A large, vigorous, semi-upright tree.
2. Regular and heavy production of medium size fruit.
3. Mature fruit has firm flesh, good shelf life and shipping quality.
4. Fruit with excellent flavor and eating quality.
5. Fruit with an attractive red skin color.
6. The fruit becoming fully tree ripe while maintaining firm flesh with a good balance between acid and sugar.
7. Flavor of fruit being distinctively different, a blend between plum and apricot with a lingering after taste.
8. Fruit with high soluble solids (brix) averaging approximately 18 degrees on the refractometer.
9. Fruit maintaining firmness on tree for approximately 2 weeks after maturity.
10. Precocious production of fruit, usually producing fruit in the second year after planting.

1 Drawing Sheet

ORIGIN OF THE VARIETY

The new and distinct variety of interspecific tree was originated by us in our experimental orchard located near Modesto, Calif. as a first generation cross between two selected seedlings with the field identification numbers 29EB30 and 42GA580. The female parent with the field identification number 29EB30 was a selection that originated from a cross between Mariposa Plum (U.S. Plant Pat. No. 111) and a selected plum-cot seedling which originated from an open pollinated Red Beaut Plum (U.S. Plant Pat. No. 2,539) seed. The pollen parent with the identification number 42GA580 is a plum-cot selection which originated as a seedling from seed of an open pollinated Red Beaut Plum tree that had been grown from budwood which had been irradiated with cobalt. A large group of these interspecific seedlings were planted and grown under careful observation, one such seedling which is the present variety, having especially desirable fruit characteristics, one of which is excellent flavor, was selected for asexual reproduction and commercialization.

ASEXUAL REPRODUCTION OF THE VARIETY

Asexual reproduction of the new and distinct variety of interspecific tree was perform by budding in our experimental orchard located near Modesto, Calif. and shows that all the characteristics of the new interspecific variety come true to the original tree and are established and transmitted through succeeding propagations.

SUMMARY OF THE VARIETY

The new and distinct variety of interspecific tree is of medium to large size, vigorous, semi-upright growth and a regular and productive bearer of medium size, firm, semi-freestone fruit with excellent flavor and eating quality. The firm crisp flesh having a distinctive flavor of a blend between plum and apricot with a desirable lingering after taste. The fruit has a good balance between sugar and acid with the soluble solids (brix)

averaging approximately 18 degrees. The fruit is also characterized by holding firm on the tree for two weeks after maturity with good storage and shelf life. The present variety of interspecific tree grows similar to a plum tree except that it is slightly less upright in growth, has a more rough bark condition throughout the tree and the flowers are somewhat larger than most plum flowers.

PHOTOGRAPHS OF THE VARIETY

The accompanying photographic illustrations are in color and show typical specimens of the foliage and fruit of the present interspecific variety, with the upper surface of the leaves being shown and the exterior and sectional view of the fruit, with a fruit being divided on its suture plane to reveal flesh coloration and a stone remaining in place. The photographs were taken shortly after being picked at maturity (firm ripe) and the colors are as nearly true as is reasonably possible in a color representation of this type.

DESCRIPTION OF THE VARIETY

The following is a detail botanical description of the present variety of interspecific tree, its flowers, foliage and fruit as based on observations of specimens grown at Modesto, Calif. with color definitions (except those in common terms) referenced to Reinhold Color Atlas by A. Kornerup and J. H. Wanscher.

Tree:

*Size.*—Medium to large.
*Vigor.*—Vigorous.
*Form.*—Semi-upright.
*Density.*—Medium dense.
*Productivity.*—Productive.
*Bearing.*—Regular, precocious.

Trunk:

*Size.*—Medium stocky.
*Surface.*—Medium shaggy.

*Color.*—Brown to grayish brown (5-E-5) to (5-E-4).

Branches:

*Size.*—Medium.

*Surface.*—Medium rough.

*Lenticels.*—Medium number — small size.

*Color.*—Bronze brown to linoleum brown (5-E-5) to (5-E-7).

Leaves:

*Size.*—Large. Average length — 4½". Average width — 1½".

*Surface.*—Smooth.

*Petiole.*—Average length — ⅝". Average thickness — 3/32".

*Form.*—Oblanceolate. Tip-acuminate.

*Margin.*—Crenate to serrulate.

*Glands.*—Average number 2, varies from 1 to 5. Globose. Medium Size. Positioned on base of leaf blade and upper portion of petiole.

*Color.*—Upper surface — green to dark green (27-E-6) to (27-F-6). Lower surface — green to dull green (27-D-5) to (27-E-5).

Flower buds:

*Blooming period.*—Date of first bloom — Mar. 6, 1990. Date of full bloom — Mar. 14, 1990. Varies slightly with climatic conditions.

*Size.*—Large.

*Color.*—White.

*Pollen.*—Scant; tree is believed to be substantially self-unfruitful.

Fruit:

*Maturity when described.*—Firm ripe.

*Date of first picking.*—Aug. 5, 1990.

*Date of last picking.*—Aug. 13, 1990.

*Size.*—Medium. Average diameter axially — 2⅜". Average transversely in suture plane — 2⅜".

*Form.*—Nearly globose — only slightly larger at apex and flattened at stem end.

*Suture.*—Shallow-extends from base to apex.

*Base.*—Slightly retuse.

*Apex.*—Rounded to slightly extended.

*Cavity.*—Size — small. Rounded to slightly elongated in suture plane. Average depth — ⅜". Average breadth — ⅜".

*Stem.*—Average length — ½". Average width — 5/32".

Skin:

*Thickness.*—Medium.

*Texture.*—Medium — tenacious to flesh.

*Down.*—Wanting.

*Bloom.*—Moderate.

*Tendency to crack.*—Slight.

*Color.*—Yellow ground color (5-A-4) to (5-A-5). Overspread with red to lake red (9-B-8) to (9-C-8) except in small areas, randomly spaced showing a speckling of yellow ground color.

Flesh:

*Ripens.*—Evenly.

*Flavor.*—Excellent, mild, sweet, a mixed blend between apricot and plum with a good balance between sugar and acid, distinctively different from either parent.

*Texture.*—Firm.

*Fibers.*—Medium number — tender.

*Juice.*—Moderate.

*Aroma.*—Slight.

*Eating quality.*—Excellent.

*Color.*—Pale yellow to pale orange (4-A-4) to (5-A-4) next to pit cavity, blending toward orange red to lake red (8-C-8) to (9-C-9) as the distance increases toward the surface. Pit cavity brownish orange (8-B-7).

Stone:

*Type.*—Semi-clingstone. Flesh adheres only in partial areas, usually along apex and ventral edge.

*Size.*—Medium. Average length — 1". Average width — ⅝". Average thickness — 5/16".

*Form.*—Ovid.

*Sides.*—Equal to unequal.

*Ridges.*—Slight ridges across the surface of the stone on each side of the suture plane.

*Surface.*—Slightly pitted throughout.

*Apex.*—Acuminate.

*Base.*—Rounded to straight.

*Tendency to split.*—None.

*Color.*—Varies from light brown to grayish brown (5-B-5) to (6-B-5).

Use: Dessert.

*Market.*—Local and long distance.

Keeping quality: Good.

Shipping quality: Good.

The interspecific tree, its flowers, foliage and fruit, herein described, may vary in slight detail due to climatic, soil and cultural practices under which the variety maybe grown; the present botanical description is that of the variety grown under the ecological conditions prevailing near Modesto, Calif.

We claim:

1. A new and distinct variety of interspecific tree, substantially as illustrated and described, characterized by its medium to large size, vigorous, semi-upright growth and a productive and regular bearer of medium size fruit with excellent flavor and eating quality; the fruit is further characterized with having flavor that is distinctively different, being a blend between apricot and plum, having firm flesh with good handling and shipping quality and holding firm on the tree approximately two weeks after maturity.

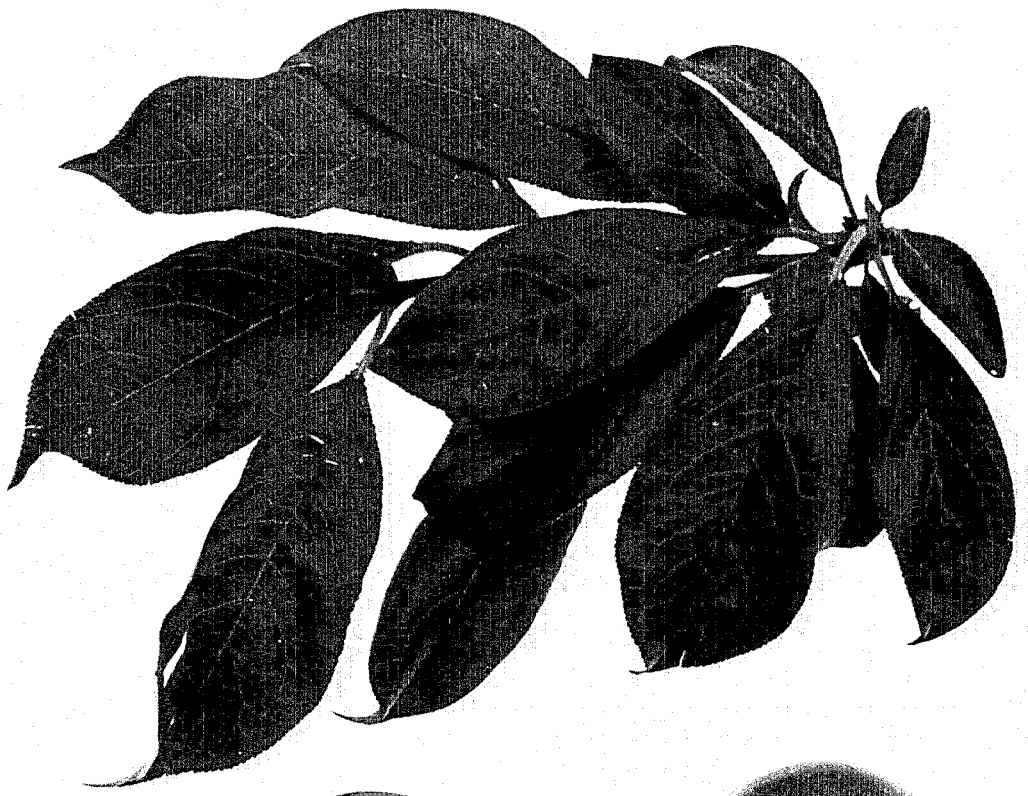
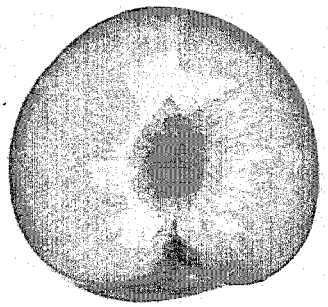
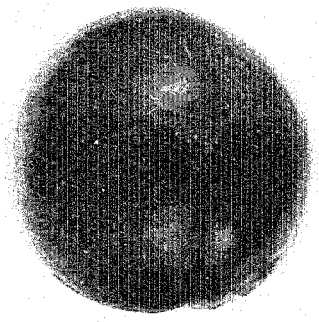
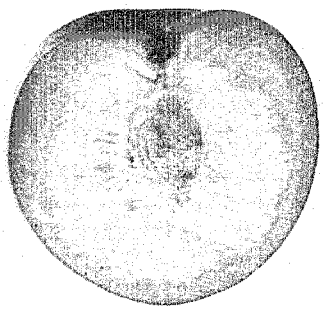
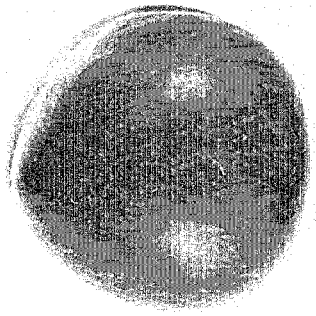

* * * * *